United States Patent
Powers

[19]

[11] Patent Number: 5,968,766
[45] Date of Patent: *Oct. 19, 1999

[54] METHOD AND APPARATUS FOR SENSING THE PRESENCE OF MICROBES

[75] Inventor: Linda Powers, Logan, Utah

[73] Assignee: B.E. Safe, Logan, Utah

[ * ] Notice: This patent is subject to a terminal disclaimer.

[21] Appl. No.: 09/052,460

[22] Filed: Mar. 31, 1998

[51] Int. Cl.[6] .............................. C12Q 1/02; C12Q 1/00
[52] U.S. Cl. .................. 435/29; 435/4; 435/283.1; 435/285.2
[58] Field of Search ............... 435/29, 4, 283.1, 435/285.2

[56] References Cited

U.S. PATENT DOCUMENTS

| | | | |
|---|---|---|---|
| 5,401,412 | 3/1995 | Yang et al. | 210/614 |
| 5,466,604 | 11/1995 | Yang et al. | 435/286.1 |
| 5,760,406 | 6/1998 | Powers | 250/461.2 |

Primary Examiner—Louise N. Leary
Attorney, Agent, or Firm—Rockey, Milnamow & Katz, Ltd.

[57] ABSTRACT

Method and apparatus for the detection of aerobic microbes on non-living surfaces in which electromagnetic radiation having a wavelength greater than 350 nm is directed onto the surface to cause excitation of pyridine nucleotides present in microbial cells to emit radiation having a higher wavelength. That higher wavelength radiation and reflected radiation is then sensed as a measure of the amount of microbial cells on the surface.

22 Claims, 3 Drawing Sheets

FIG.3
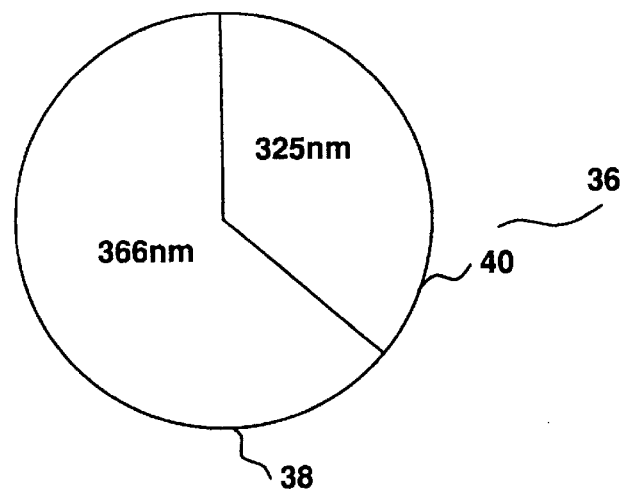
FIG.4
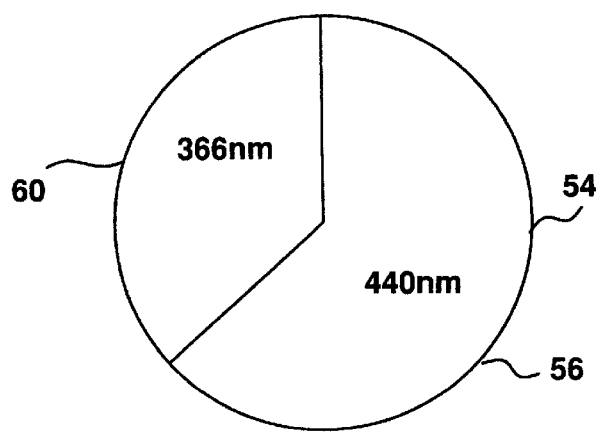
FIG.5

METHOD AND APPARATUS FOR SENSING THE PRESENCE OF MICROBES

This invention relates to a method and apparatus for sensing the presence of microbes on a non-living surface, and more particularly to a method and apparatus for sensing the presence of microbes in meat, poultry and the like.

BACKGROUND OF THE INVENTION

It is of course elementary that all aerobic microbial cells produce energy for the cell through respiration. As cellular respiration occurs, pyridine nucleotides are reduced in the living cells. That reduction can be detected by exciting the microbial cells with electromagnetic radiation in the UV range, and forms a basis for detection of cellular respiration.

In U.S. Pat. No. 4,162,405, which issued on Jul. 24, 1979, there is described a method and apparatus for measuring heterogeneity of oxygen delivery in human and animal tissue. The foregoing patent indicates that it is possible to detect and distinguish reduced nucleotides such as nicotinamide adenine nucleotides or NADH occurring in, for example, brain tissue and other living tissues by means of fluorescence.

With recent announcements of bacterial contamination in meats and poultry, there has been a need to provide a method and apparatus which can be used to detect such microbial contamination in meat and poultry which can be operated inexpensively and rapidly in, for example, meat and poultry production facilities. In U.S. Pat. No. 4,631,413, there is described a technique for examining the surface of meats, fish and the like for bone, fat and cartilage. Cartilage and bone fluoresce at about 390 nm when excited with electromagnetic energy or lightwaves having a wavelength of about 340 nm. The bone, cartilage and connective tissue from some animals, and notably pigs and chicken, exhibit weak fluorescence at about 455 nm; cow fat exhibits weak fluorescence at about 475 nm. The foregoing patent shows that cow meat has essentially no fluorescence in the vicinity of about 440 nm.

Thus, the foregoing patent does not disclose or suggest any technique by which the presence of living microbes exhibits fluorescence around 440 nm with excitation around 366 nm and can be distinguished from meat and poultry tissue which is no longer living.

It is accordingly an object of the invention to provide a method and apparatus which can be used in the detection of microbial contamination in non-living surfaces such as meat and poultry.

It is a more specific object of the invention to provide a method and apparatus for use in the detection of microbial contamination in meat and poultry in which microbial contamination can be determined inexpensively and rapidly in, for example, meat and poultry production facilities.

It is yet another object of the invention to provide a method and apparatus for use in the detection of microbial contamination in meat and poultry in which the fluorescence of reduced nucleotides are excited by electromagnetic radiation to distinguish the metabolic reactions of microbes from the tissue of meat and poultry to allow microbial contamination in meat and poultry to be determined without contact with the meat or poultry.

SUMMARY OF THE INVENTION

The concepts of the present invention reside in a method and apparatus for the detection of microbes on a non-living surface such as meat and poultry in which electromagnetic energy having wavelengths greater than about 350 nm are directed toward a meat and/or poultry sample. The electromagnetic radiation thus excites the microbial cells present on the meat or poultry surface, causing the microbes to emit florescence having a wavelength higher than that of the excitation wavelength. Thus, the microbial cells present on the surface of the meat or poultry and specifically the NADH contained therein emit detectable fluorescence. At the same time, the non-living surface reflects or scatters at least some of the electromagnetic radiation. The presence of living microbial cells is determined by sensing both the fluorescence from the cell respiration and the electromagnetic radiation reflected or scattered by the surface.

Thus, the method and apparatus of the present invention provides an inexpensive and rapid way in which to rapidly scan meat and poultry products to detect and measure the presence of microbial contamination without introducing further contamination.

In accordance with another embodiment of the invention, it is possible, and sometimes desirable, to direct electromagnetic radiation having a wavelength greater than about 350 nm as well as electromagnetic radiation having a lower wavelength which has the capability of exciting another characteristic of the meat or poultry sample (such as the fat content). Thus, in accordance with this embodiment of the invention, it is possible not only to detect microbes present in the sample, but other characteristics as well. For example, use can be made of wavelengths below 350 nm, specifically wavelengths of about 320–325 nm which have the capability, as is known in the art, to excite fat molecules and allow the fat content of the meat or poultry sample to be determined along with the microbial content.

In accordance with this form of the invention, it is frequently desirable to utilize a light source emitting electromagnetic radiation over both wavelengths, that is wavelengths above and below 350 nm. In accordance with the present form of the invention, the light emitted by the light source is sequentially filtered to pass therethrough electromagnetic radiation of a wavelength sufficient to excite NADH in the cells and then emit light sufficient to excite fat in the meat and poultry sample. By controlling the frequency at which the two different wavelengths of electromagnetic radiation are directed to the sample, it is possible to modulate the signal in time so that the phase of the signal is specific to the microbial content and fat content, respectively.

It has also been found that by rapidly changing the electromagnetic radiation directed to the sample at frequencies different than 60 Hertz, the effects of ambient light (and particularly fluorescent light) can be substantially minimized. The modulation of the signal also permits the use of the sensor which can be moved to direct the electromagnetic radiation to various parts of an animal carcass without substantially affecting the accuracy of the measurement of either microbial content or fat content.

In accordance with the practice of the invention, a sensor is used to detect not only the fluorescence generated by the NADH but also to detect the reflected electromagnetic radiation. That serves to normalize the signal and compensate for variations in the signal that might otherwise be caused by the use of varying distances between a probe and the sample being scanned and variations between different surfaces.

BRIEF DESCRIPTION OF THE DRAWINGS

FIG. 3 is an illustration of one embodiment of a filter wheel employed for excitation in the practice of the present invention as schematically illustrated in FIG. 2.

FIG. 4 is an illustration of one embodiment of a filter wheel employed for emission complimentary to the filter wheel illustrated in FIG. 3.

FIG. 5 is a timing diagram illustrating the operation of the excitation filter shown in FIG. 3 and the emission filter shown in FIG. 4.

DETAILED DESCRIPTION OF THE INVENTION

Figure 1:
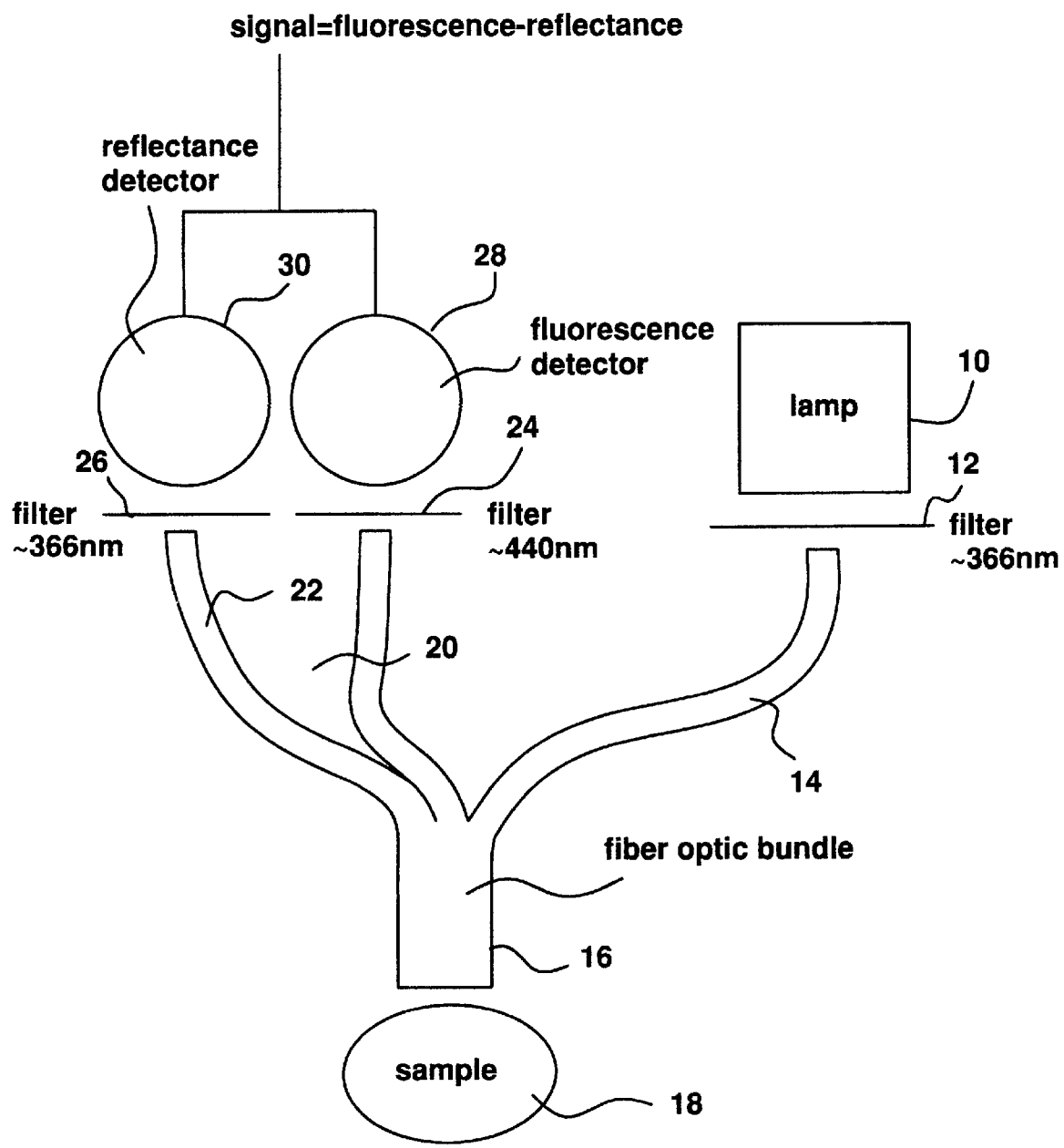
FIG. 1 is a schematic view illustrating one embodiment of the invention.

One embodiment of the invention is illustrated in FIG. 1 of the drawings. That drawing illustrates, in schematic form, a microbe sensor of the invention which includes a source of light 10 which is rich in electromagnetic radiation having wavelengths less than about 400 nm. As will be appreciated by those skilled in the art, the source of electromagnetic radiation 10 can be any of a variety of devices which produce UV light having wavelengths less than about 400 nm. The source of electromagnetic radiation 10 can be a laser or various types of lamps which emit electromagnetic radiation within the UV range as are commercially available.

The wavelength of light emitted by the source 10 is chosen by a filter 12, preferably in the form of a narrow band-width filter which passes electromagnetic radiation having wavelengths within the desired range. In general, when seeking to excite NADH in the microbes, the filter 12 should be one which emits electromagnetic radiation within the range of about 350 to 390 nm, and preferably with a peak of about 366 nm.

Positioned to receive the light emitted from the light source 10 through filter 12 is a conduit for electromagnetic radiation 14, preferably in the form of a fiber optic element or bundle of elements capable of conducting the electromagnetic energy passing from the source 10 through the filter 12. The fiber optic bundle terminates in a probe 16, which is preferably a hand-held probe which can then be used to scan, either manually or under automated control, a sample 18 of meat or poultry to determine whether such meat or poultry contains microbial contamination. As will be appreciated by those skilled in the art, the probe 16 simply represents the distal end of the fiber optic element 14 and thus transmits electromagnetic radiation which has been generated by the source 10 and passed through the filter 12 so that the electromagnetic radiation strikes the sample 18 to effect excitation of NADH in any living microbial cells contained on that sample.

Also contained within the probe are a pair of other fiber optic elements or bundles 20 and 22 as shown in FIG. 1. Each of those fiber optic elements are thus positioned to transmit electromagnetic radiation from the sample for detection. In the embodiment illustrated in FIG. 1, fiber optic element 20 conveys electromagnetic energy from the sample to a filter 24; that filter is chosen to pass electromagnetic radiation having the wavelength of the fluorescence generated in the microbial cells present in the sample 18. In general, use should be made of filters for the fluorescence capable of passing wavelengths within the range of about 400 to about 480 nm, and preferably peaked about 440 nm. As is known to those skilled in the art, where NADH is excited with electromagnetic energy having a wavelength of about 366 nm, the fluorescence generated in the mitochondria by the NADH has a peak wavelength of about 440 nm.

It is also desirable, in the practice of the invention, to use another filter 26 associated with fiber optic element 22 which passes only electromagnetic radiation having substantially the same wavelength as the electromagnetic radiation directed to the sample through fiber optic element 14. Thus the filter 26 should pass electromagnetic radiation within the range of 350–390 nm, and preferably peaked at about 366 nm.

The apparatus as illustrated in FIG. 1 also includes a pair of detector elements 28 and 30 which detect electromagnetic radiation passing through filters 24 and 26, respectively. As will be appreciated by those skilled in the art, the detectors 28 and 30 employed in the practice of the present invention are elements which are sensitive to electromagnetic radiation, converting that radiation into an electrical signal which is proportional to the intensity of the radiation presented to the detectors through filters 24 and 26, respectively. A number of conventional devices can be used for that purpose, and includes photodiodes, photomultiplier tubes, video cameras, charge couple devices as well as a host of other detectors of electromagnetic radiation well known to those skilled in the art.

Thus, detector 28, because the electromagnetic radiation passed through the associated filter 24 is essentially limited to the wavelength of electromagnetic energy associated with the fluorescence of NADH, measures the amount of fluorescence due to NADH passed through the filter 24 from the sample 18 and detected by the detector. The electromagnetic radiation passed through fiber optic element 22 is filtered to pass only electromagnetic radiation having a wavelength substantially the same as that of the electromagnetic energy directed onto the surface of the sample, it measures only the reflectance of the surface of the meat or poultry sample on which microbial contamination may be found. Both sensors 28 and 30 thus convert the electromagnetic energy to a corresponding electrical signal, and the sample signal is determined by subtracting the electromagnetic radiation passing through the filter 26 to the detector 30 of reflected electromagnetic radiation from the sample 18 from the amount of electromagnetic radiation passing through filter 24 to detector 28 representing NADH fluorescence.

As was explained above, by comparing the fluorescence signals to the reflected signals, the system normalizes the signals to compensate for variations in the distance of the probe 16 from the surface of the sample 18 and variations between different surfaces.

Thus, in use, the probe 16, preferably in the form of a hand-held probe, can be positioned adjacent to a surface of the sample 18 and electromagnetic energy from the source 10, filtered by the filter 12, is directed onto the surface. The wavelength of the radiation thus causes excitation of any living microbial cells undergoing cellular respiration, and generates fluorescence as well as reflected radiation. The light thus generated or reflected by the surface of the sample 18 and conveyed through fiber optic elements 20 and 22 is filtered by filters 24 and 26, respectively. In that way, detector 28 detects the electromagnetic radiation created by fluorescence of NADH while detector 30 measures electromagnetic radiation having the same wavelength as the radiation directed onto the surface as a measure of the reflectance of the surface. The difference between those two signals from detectors 28 and 30 is thus a normalized measure of the amount of fluorescence generated on the surface of the sample. That, in turn, is a measure of the amount of live microbial cells present on the surface.

That difference or ratio signal can be used in different ways. For example, the difference or ratio signal can be used to select from a look-up table the concentration of living microbial cells on the surface of the sample as has been established by calibration. Alternatively, the difference or ratio signal can also be supplied to a microprocessor programmed to calculate the concentration of living microbial cells on the surface from information established by calibration. As will be appreciated by those skilled in the art, it is also possible and sometimes desirable to scan one or more surfaces of the sample 18 to determine the average amount or distribution of microbes on the surfaces of the sample. Various techniques for scanning the sample are known in the prior art. One such technique is that disclosed by Chance et al. in U.S. Pat. No. 4,162,405, the disclosure of which is incorporated herein by reference. In the apparatus there disclosed, use can be made of one or more light sources, each of which can be electromechanically scanned across the sample to be examined by means of electromagnetically driven mirrors on the X and Y axes. The mirrors are thus programmed to provide a raster type of illumination as disclosed in the foregoing patent.

The fluorescence created by the NADH present in the microbial cells during cellular respiration can be readily distinguished from the animal tissue forming the meat or poultry sample. To ensure that the microbe sensor of the present invention has the capability of distinguishing between fluorescence due to NADH as compared to the type of fluorescence normally found in animal carcasses, the wavelength of the electromagnetic radiation should be controlled within the range as described so that only the fluorescence arising from cellular respiration and NADH is detected by detector 28. The cells of the animal carcass, because those cells cease cellular respiration shortly after slaughter, do not contribute appreciably to fluorescence arising from cellular respiration which is sensed by the microbial sensor of the present invention. While the concepts of the present invention are particularly well suited for use in the detection of microbes on the surface of meat and poultry, it will be understood that the concepts of the present invention can likewise be used to detect microbial cellular respiration on other surfaces, so long as those other surfaces are not metabolizing by cellular respiration.

Figure 2:
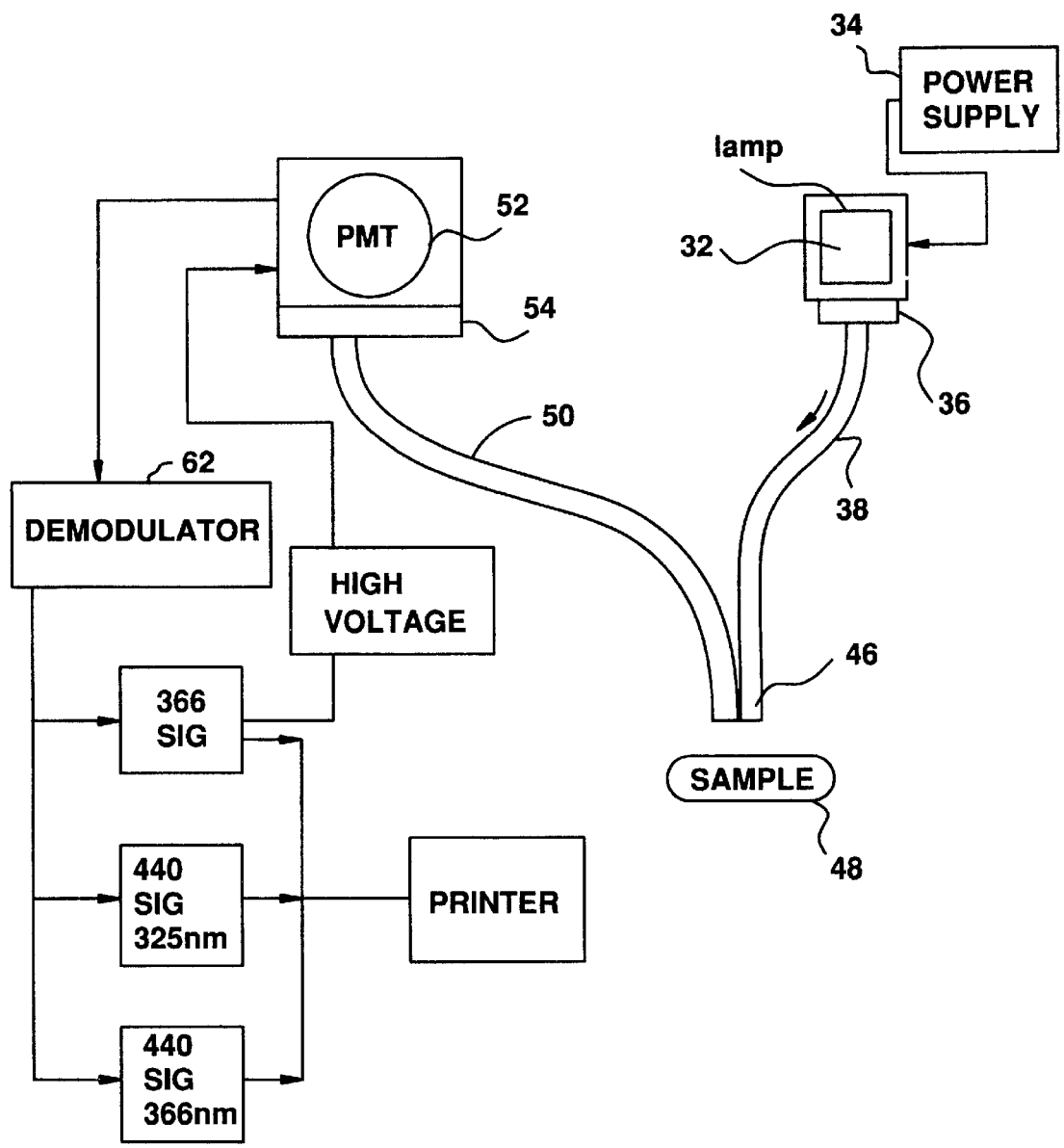
FIG. 2 is a schematic illustration of yet another embodiment of the invention.

An alternative embodiment of the invention is illustrated in FIGS. 2 and 3 of the drawings. As is best shown in FIG. 2, the device there described includes a source 32 of electromagnetic radiation which is powered by a suitable power supply 34. Associated with the source 32 of electromagnetic radiation is a filter 36 which is perhaps more fully described in FIG. 3 of the drawings. As can be seen in FIG. 3, the excitation filter 36 is divided into at least two filter elements, one having the capability of passing electromagnetic radiation which excites NADH fluorescence thereon, and preferably passes electromagnetic radiation having a wavelength within the range of 350–390 nm. Best results are usually obtained when the filter passes electromagnetic radiation having a wavelength of about 366 nm. The other filter element of filter 36 is a segment passing electromagnetic radiation having a wavelength within the range of 305 to 340 nm, preferably peaking around 325 nm, to excite fat present on the surface of the sample.

In a preferred embodiment of the invention, the filter wheel 36 includes a segment having the capability of passing electromagnetic radiation of a wavelength of about 300–340 nm and preferably peaked about 325 nm to stimulate fluorescence of fat present on the surface of the sample. As can be seen in FIG. 3, one typical illustration of the configuration of the excitation filter wheel 36 is that it can be divided into two segments 38 and 40. Segment 38 passes electromagnetic radiation having a wavelength of about 366 nm while segment 40 passes electromagnetic radiation having a wavelength of about 325 nm. As illustrated in FIG. 3, the segment of the filter 36 passing electromagnetic radiation having a wavelength of about 325 nm in the form of an arcuate segment representing about 120 degrees of the circular filter 36, while the remainder is an arcuate segment transmitting light at 366 nm and represents about 240 degrees of the filter element 36. As will be appreciated by those skilled in the art, the present invention is not limited to those particular segments.

Referring to the timing diagram or FIG. 5, the electromagnetic radiation transmitted through the filter 36 has a wavelength of 325 nm from time T1 to time T2. While the electromagnetic radiation transmitted to the sample having a wavelength of 366 nm occurs from time T2 to time T4 in proportion to the number of degrees represented by each of the segments 40 and 38 making up filter wheel 36.

It will be understood, however, that the concepts of the present invention are not limited to any particular filter wheel configuration. For example, it is possible to employ a filter wheel having equal segments, one passing electromagnetic radiation having a wavelength of 366 nm and one passing electromagnetic radiation having a wavelength of 325 nm. More or fewer segments may be employed, depending upon the design criteria selected for the filter wheel.

Alternatively, it is not essential to use rotating filters as illustrated above. It is also possible to employ two filters positioned side by side between a source of electromagnetic radiation such as a lamp and the fiber optic elements transmitting electromagnetic radiation to the sample. Other methods include vibrating filters or electro-optic devices. As will be appreciated by those skilled in the art, any technique which changes the wavelength between about 366 nm and about 325 nm may be employed in the practice of the invention. The lamp can thus be pulsed to generate the desired time modulation of the wavelength of electromagnetic radiation.

Returning to FIG. 2, the electromagnetic energy emitted by the source 32 is thus filtered by the excitation filter wheel 36 which generates electromagnetic radiation having wavelengths of about 366 nm for a predetermined period of time and then electromagnetic radiation having a wavelength of about 325 nm for another predetermined period of time. As will be appreciated by those skilled in the art, it is not essential that the segments be equal; it is possible, and sometimes desirable, to design the filter wheel 36 such that the time period during which electromagnetic radiation having a wavelength of 366 nm is either greater than or less than the time period during which electromagnetic radiation having a wavelength of 325 nm is used.

Nonetheless, the two alternating wavelengths of light from the filter wheel 36 are passed through a fiber optic or other optical element 38 through which the two wavelengths of light, staggered or modulated in time, are directed to a probe 46 and onto the surface of a sample 48. The electromagnetic energy having a wavelength of about 366 nm thus excites NADH of any microbial contamination present on the surface of the sample. That in turn causes the microbial cells to exhibit fluorescence at about 440 nm. The electromagnetic radiation having a wavelength of about 325 nm selectively excites any fat cells present on the surface of the sample. Those fat cells exhibit fluorescence at 440 nm. And finally, the surface of the sample also reflects electromagnetic energy having the wavelength of 366 nm for 366 nm excitation and 325 nm for 325 nm excitation. Either wavelength could be used for the normalization provided by the present invention; thus the illustration of a normalization based on reflected electromagnetic energy at 366 nm was provided as an example.

Thus, the sample emits, in accordance with the phase of the excitation filter wheel, reflected electromagnetic energy at 366 nm and 325 nm, fluorescence of NADH at 440 nm from excitation of microbial cells at 366 nm and fluorescence from fat cells at 440 nm due to excitation with electromagnetic energy having a wavelength of 325 nm. The electromagnetic energy emitted by the sample 48 are collected by the probe 46 and transmitted by means of fiber optic or other optical elements 50 to detector 52 such as a photomultiplier tube. As with the embodiment shown in FIG. 2, other devices known in the art for detecting electromagnetic radiation may likewise be used. Similarly, it should be understood by those skilled in the art that it is not essential in the practice of the present invention to employ fiber optics as illustrated in the preferred embodiment inasmuch as such fiber optic elements are a convenient way of transmitting electromagnetic radiation. As those skilled in the art will understand, transmission of electromagnetic radiation can also be accomplished through ambient air by simply positioning the source of electromagnetic radiation, the filters and detectors in the appropriate positions. Alternatively, use can also be made of other electromagnetic radiation carriers such as quartz rods.

The detector can likewise be provided with a rotating emission filter 54 having segments corresponding to the segments of the filter 36 and is rotated in synchronism therewith. As shown in FIG. 4, when use is made of a filter having the configuration as shown in FIG. 3, the filter associated with the detector 52 can likewise have two segments. As shown in FIG. 4, the filter 54 has a segment 56 capable of transmitting electromagnetic energy having a wavelength of about 440 nm and has an arcuate segment of about 240 degrees. As the corresponding segment 38 of the filter 36 transmits electromagnetic energy having a wavelength of 366 nm, that energy excites the microbial cells, and specifically the NADH therein, to exhibit fluorescence at 440 nm which is then passed through the corresponding segment 56 of emission filter 54 as a measure of the microbial contamination on the surface of the sample. Because the filters 36 and 54 are rotated in synchronism, the electromagnetic energy passed through segment 40 of filter 36 having a wavelength of about 325 nm excites the fluorescence of fat cells, if any, in the sample, causing them to emit fluorescence at 440 nm which then passes through the segment 56 as a measure of the fat content of the sample.

The segment 60 of filter 54 can be provided with a filter having the capability of transmitting electromagnetic radiation at 366 nm or 325 nm (or both) and having an arcuate segment corresponding to about 120 degrees as illustrated in FIG. 4. The corresponding segment in filter 36 emits radiation at substantially the same wavelength and thus segment 60 of filter 54 transmits to the detector 52 electromagnetic energy having the same wavelength as the original excitation radiation for microbial cells. That in turn allows the detector 52 to determine the amount of electromagnetic radiation having a wavelength of 366 nm or 325 nm (or both) reflected by the sample.

Thus, the photomultiplier tube emits three timemodulated signals, one signal at 366 nm or 325 nm (or both) which is demodulated by the demodulator 62 representing the amount of the reflected light, a signal demodulated by demodulator 62 having a wavelength of 440 nm from the excitation wavelength of 325 nm as a measure of the fat content and a signal representing the amount of light emitted at 440 nm demodulated in demodulator 62 arising from the excitation wavelength of about 366 nm as a measure of the microbial content. Those three signals can thus be processed in any of a variety of conventional ways to determine the fat content and the microbial content of the sample (e.g. direct calibration).

Referring again to the timing diagram of FIG. 5, the electromagnetic radiation transmitted to the sample through excitation filter 36 has a wavelength of 325 nm for about 120 degrees of revolution of the excitation filter 36. Because the emission filter 54 passes electromagnetic radiation in the same time period having a wavelength of 440 nm, the time interval corresponding to the first 120 degrees of revolution of excitation filter wheel 36, from time T1 to T2 as shown in FIG. 2, the signal over that time interval is a measure of the fat content of the sample. For the next 120 degrees of rotation of the excitation filter 36 and the emission filter 54, the electromagnetic radiation exciting the sample has a wavelength of 366 nm while the electromagnetic radiation emitted from the sample has a wavelength of 440 nm for the time interval of T2 to T3 in FIG. 5. The signal over that time interval is related to the microbial content of the sample, and specifically the fluorescence of NADH excited at 366 nm and emitted at 440 nm. The final 120 degrees of revolution of the excitation filter 36 and the emission filter 54 transmit to the sample and receive therefrom electromagnetic radiating having a wavelength of 366 nm for time interval T3 to T4 as shown in FIG. 5. That signal is thus related to the electromagnetic radiation reflected by the sample.

As will be appreciated by those skilled in the art, just as it is not necessary to employ a filter wheel associated with the source of electromagnetic radiation, it is likewise not necessary to employ a rotating emission filter 54 with the detector for electromagnetic radiation. For example, it is possible and sometimes desirable to employ three different detectors like those shown in FIG. 1, each one of which is equipped with an appropriate filter. In that embodiment, two of the detectors have filters transmitting electromagnetic radiation having wavelengths of 440 nm and 366 nm are used with a source of electromagnetic radiation emitting at 366 nm. The third detector having a filter transmitting electromagnetic radiation at 440 nm is then used with a source of electromagnetic radiation emitting radiation having a wavelength of 325 nm. In general, it is preferred to employ-rotating filters to ensure that the sources of electromagnetic radiation and their corresponding detectors sample the same area of the sample as distinguished from adjacent areas.

One of the advantages of the use of a rotating filter wheel in accordance with the embodiment illustrated in FIGS. 2–4 is that a rapidly rotating filter wheel substantially eliminates or minimizes the effect of ambient light, and especially fluorescent light, on the accuracy of the measurements being made. As will be appreciated by those skilled in the art, by rotating the filter wheels at speeds sufficient to create a frequency above 75 Hertz (Hz), the effects of ambient light operating at a frequency of 60 Hz and multiples thereof is substantially eliminated.

It is also preferred in the practice of the present invention, as schematically illustrated in FIG. 2 of the drawing, to include voltage feedback to the detector 52. The use of such a voltage feedback maintains the signal at 366 nm substantially constant by adjusting the voltage to, for example, the photomultiplier tube 52. That ensures that the readings by the photo detector are substantially normalized. In addition, if a bright light is accidentally exposed to the probe 16, the feedback to the photomultiplier tube 52 adjusts its voltage downwardly to avoid damage to the photomultiplier tube. Because that voltage has an upper limit, that photomultiplier tube is not damaged when no light is present.

As will be appreciated by those skilled in the art, various changes and modifications can be made in the details of construction, operation and use without departing from the spirit of the invention especially as defined in the following claims.

What is claimed is:

1. A method for the detection of microbes in an environment comprising the steps of:
    (a) directing electromagnetic waves into an environment, said electromagnetic radiation having a wavelength greater than 350 nm, whereby any microbial cells present in the environment and containing nicotinamide adenine pyridine nucleotides are excited to emit fluorescence having an energy less than the excitation energy and whereby some of said electromagnetic radiation is reflected in said environment, and
    (b) sensing the fluorescence and the reflected electromagnetic radiation as a measure of the amount of microbes present in said environment.

2. The method is defined in claim 1 wherein the electromagnetic radiation having a wavelength within the range of about 350 to 400 nm.

3. The method is defined in claim 1 wherein the electromagnetic radiation having a peak wavelength of about 366 nm.

4. The method is defined in claim 1 which includes the step of filtering the electromagnetic radiation emitted by the microbial cells to isolate a narrow band of wavelengths.

5. The method is defined in claim 1 wherein the electromagnetic radiation emitted by the microbial cells is filtered to provide a peak wavelength of about 440 nm.

6. The method as defined in claim 1 wherein the electromagnetic radiation has a wavelength greater than about 350 nm to cause fluorescence of microbes in said environment and wherein the fluorescence exhibits a wavelength greater than about 400 nm.

7. The method as defined in claim 1 which includes the steps of directing electromagnetic radiation having two wavelengths, one of said wavelengths being greater than about 350 nm and the other of said wavelengths being less than about 340 nm, whereby the higher wavelength excites fluorescence of microbial cells and the lower wavelength excite fluorescence of another component present in the environment.

8. The method as defined in claim 1 wherein the environment is a meat or poultry surface and the electromagnetic radiation directed thereto have one wavelength greater than about 350 nm to cause fluorescence of microbial cells present on the surface and another wavelength less than about 340 nm to excite fluorescence of fat, cartilage or bone present on the surface of the sample.

9. The method as defined in claim 1 which includes the step of sensing the fluorescence of microbial cells and sensing the electromagnetic radiation reflected by said environment and determining the difference or ratio therebetween as a measure of the amount of microbes present in said environment.

10. The method as defined in claim 1 which includes the step of filtering the electromagnetic radiation directed into the environment to provide a narrow band of wavelengths of said electromagnetic radiation directed into the environment.

11. The method as defined in claim 1 wherein the electromagnetic radiation directed into the enviroment is filtered to provide a peak wavelength of about 366 nm.

12. The method as defined in claim 1 which includes the step of rotating a rotary filter to filter the electromagnetic radiation directed into the environment to generate timed pulses of electromagnetic radiation directed into the environment having two discrete bands of wavelengths, one of said bands having wavelengths predominantly greater than 350 nm and the other of said bands having wavelengths predominantly less than 340 nm whereby said one band excites the fluorescence of microbial cells present in the environment and said other band excites the fluorescence other substances present.

13. The method as defined in claim 1 which includes the step of rotating a rotary filter to filter the electromagnetic radiation emitted from said environment to receive timed pulses of electromagnetic radiation having two discrete bands of wavelengths, one of said bands having wavelengths predominantly above about 400 nm as a measure of the fluorescence of microbial cells and the other of said bands having energies near that of the excitation radiation as a measure of electromagnetic radiation reflected by said environment.

14. Apparatus for the detection of microbes on a non-living environment comprising:
    (a) means for directing electromagnetic radiation toward an environment, said means adapted to emit radiation having wavelengths greater than 350 nm and excite microbial cells in the environment to emit fluorescence;
    (b) a detector for electromagnetic radiation capable of converting the radiation into an electrical signal, said detector adapted to detect electromagnetic radiation at wavelengths above about 400 nm as a measure of microbial cells present in the environment and to detect electromagnetic radiation having energies near that of the excitation radiation as a measure of the electromagnetic radiation reflected by the environment; and
    (c) means for receiving electrical signals corresponding to the fluorescence of the microbial cells and electrical signals corresponding to the electromagnetic radiation reflected by the environment and determining the amount of microbes in the environment.

15. The apparatus as defined in claim 14 wherein the means for directing electromagnetic radiation is adapted to direct electromagnetic radiation of at least two discrete bands of wavelengths, one of the bands having wavelengths above 350 nm to excite the fluorescence of microbial cells and the other of the bands having wavelengths below about 340 nm as a measure of another characteristics of the environment.

16. The apparatus as defined in claim 15 wherein the means for directing electromagnetic radiation includes at least two excitation filters, one of the filters passing electromagnetic radiation having wavelengths predominantly above 350 nm and the other of the filters passing electromagnetic radiation having wavelengths predominantly below 340 nm.

17. The apparatus is defined in claim 16 wherein said filters are in the form of two arcuate segments mounted for rotation, one segment adapting to pass electromagnetic radiation having wavelengths predominantly above 350 nm and the other segment adapted to pass electromagnetic radiation having wavelengths predominantly below 340 nm whereby rotation of the filter generates timed pulses of electromagnetic radiation having wavelengths predominantly above 350 nm and electromagnetic radiation having wavelengths predominantly below 340 nm.

18. The apparatus is defined in claim 14 which includes a probe, said probe including fiber optic elements adapted to transmit excitation electromagnetic radiation from the means for directing electromagnetic radiation and fiber optic elements attached to transmit emission electromagnetic radiation from the sample to the detector.

19. The apparatus is defined in claim 14 which includes means for scanning the fluorescence signals, including means for moving said means for directing electromagnetic radiation along an X and Y axes to provide a raster illumination of the sample.

20. The apparatus as defined in claim 19 which includes at least two emission filters, one filter adapted to pass electromagnetic radiation having wavelengths predominantly above 400 nm and the other of said filters adapted to pass electromagnetic radiation having energies near that of the excitation radiation whereby the electromagnetic radiation passed through the filter having wavelengths above 400 nm corresponds to the microbial content of the environment and the electromagnetic radiation passed through the filter having energies near that of the excitation radiation corresponds to the amount of light reflected by the environment.

21. The method as defined in claim 1 wherein the electromagnetic waves are directed into the environment in time-modulated pulses.

22. The apparatus as defined in claim 17 wherein the means for directing electromagnetic radiation includes means for time-modulating the electromagnetic radiation as pulses.

* * * * *